United States Patent
Nair et al.

(10) Patent No.: US 9,353,030 B2
(45) Date of Patent: May 31, 2016

(54) ONE-STEP PROCESS FOR HEXAFLUORO-2-BUTENE

(71) Applicant: Honeywell International Inc., Morristown, NJ (US)

(72) Inventors: Haridasan K. Nair, Williamsville, NY (US); David Nalewajek, West Seneca, NY (US); Glenn Matthies, Lockport, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/737,530

(22) Filed: Jun. 12, 2015

(65) Prior Publication Data

US 2016/0023972 A1    Jan. 28, 2016

Related U.S. Application Data

(60) Provisional application No. 62/028,851, filed on Jul. 25, 2014.

(51) Int. Cl.
| C07C 17/00 | (2006.01) |
| C07C 17/361 | (2006.01) |
| C07C 17/26 | (2006.01) |
| C07C 17/358 | (2006.01) |
| B01J 23/755 | (2006.01) |
| B01J 21/18 | (2006.01) |
| B01J 23/46 | (2006.01) |
| B01J 27/132 | (2006.01) |

(52) U.S. Cl.
CPC .............. *C07C 17/361* (2013.01); *B01J 21/18* (2013.01); *B01J 23/462* (2013.01); *B01J 23/466* (2013.01); *B01J 23/755* (2013.01); *B01J 27/132* (2013.01); *C07C 17/26* (2013.01); *C07C 17/358* (2013.01)

(58) Field of Classification Search
CPC ........ C07C 21/18; C07C 21/22; C07C 17/23; C07C 17/26; B01J 21/18
USPC .................................................. 570/155, 156
See application file for complete search history.

(56) References Cited

U.S. PATENT DOCUMENTS

| 8,530,709 B2 | 9/2013 | Poss et al. |
| 8,604,257 B2 | 12/2013 | Poss et al. |
| 8,901,360 B2 | 12/2014 | Poss et al. |
| 2011/0215273 A1 | 9/2011 | Uenveren et al. |
| 2011/0237843 A1 | 9/2011 | Tung et al. |

FOREIGN PATENT DOCUMENTS

WO    WO 2010/095764 A1  *  8/2010

* cited by examiner

*Primary Examiner* — Jafar Parsa
(74) *Attorney, Agent, or Firm* — Bruce O. Bradford

(57) ABSTRACT

Disclosed is a one step process for making of 1,1,1,4,4,4-hexafluoro-2-butene. More specifically, the present invention provides a process for making hexafluoro-2-butene, continuously, from 2-chloro-3,3,3-trifluoropronene using $Fe_2O_3$/NiO impregnated carbon catalyst at 600° to 650° C.

18 Claims, No Drawings

ONE-STEP PROCESS FOR HEXAFLUORO-2-BUTENE

CROSS-REFERENCE TO RELATED APPLICATION

This application claims domestic priority from commonly owned, U.S. Provisional Patent Application Ser. No. 62/028,851, filed 25 Jul. 2014, the disclosure of which is hereby incorporated herein by reference.

BACKGROUND OF THE INVENTION

Hexafluoro-2-butene ($CF_3CH=CHCF_3$, HFO-1336) has zero ozone depletion potential (ODP) and low global warming potential (GWP) and is being used as a foam blowing agent, refrigerant and solvent. Reported methods for making HFO-1336 require multiple steps or give poor conversion or need raw materials that are not easily available. See for example, U.S. Pat. Nos. 8,426,655 and 8,530,709, and the references cited therein, the disclosures of which are hereby incorporated herein by reference. Thus, there is a continuing need to develop cost effective manufacturing processes which will circumvent the above issues regarding the production of HFO-1336.

SUMMARY OF THE INVENTION

Disclosed is a one step process for making of 1,1,1,4,4,4-hexafluoro-2-butene (HFO-1336). This includes both trans and cis (E and Z) isomers of HFO 1336.

In one embodiment, the invention is directed to a process for making 1,1,1,4,4,4-hexafluoro-2-butene (HFO-1336) from 2-chloro-3,3,3-trifluoropropene (HCFC-1233xf) comprising reacting HCFC-1233xf with a selected catalyst, at a sufficient temperature to afford HFO-1336.

In certain embodiments, the process for making 1,1,1,4,4,4-hexafluoro-2-butene (HFO-1336) is conducted in the vapor phase.

In certain embodiments, the process for making 1,1,1,4,4,4-hexafluoro-2-butene (HFO-1336) is conducted in a continuous manner.

In certain embodiments, the process for making 1,1,1,4,4,4-hexafluoro-2-butene (HFO-1336) makes use of a catalyst which comprises $Fe_2O_3/NiO$.

In certain embodiments, the process for making 1,1,1,4,4,4-hexafluoro-2-butene (HFO-1336) is conducted with the catalyst impregnated on carbon.

In certain embodiments, the process for making 1,1,1,4,4,4-hexafluoro-2-butene (HFO-1336) is conducted wherein the carbon support for the catalyst is activated carbon.

In certain embodiments, the process for making 1,1,1,4,4,4-hexafluoro-2-butene (HFO-1336) is conducted wherein the activated carbon catalyst support is granular with a mesh size of 4-14.

In certain embodiments, the process for making 1,1,1,4,4,4-hexafluoro-2-butene (HFO-1336) is conducted wherein the activated carbon support for the catalyst is pelletized.

In certain embodiments, the process for making 1,1,1,4,4,4-hexafluoro-2-butene (HFO-1336) includes a reaction temperature that ranges from 600° to 650° C.

In certain embodiments, the process for making 1,1,1,4,4,4-hexafluoro-2-butene (HFO-1336) includes formation of both the trans and cis isomers of HFO-1336.

In certain embodiments of the process for making 1,1,1,4,4,4-hexafluoro-2-butene (HFO-1336), the predominant isomer of HFO-1336 formed is the trans isomer.

In certain embodiments of the process for making 1,1,1,4,4,4-hexafluoro-2-butene (HFO-1336), the ratio of the trans isomer to the cis isomer of HFO-1336 is about 88:12.

In certain embodiments, the process for making 1,1,1,4,4,4-hexafluoro-2-butene (HFO-1336) includes a step wherein the trans isomer is converted into the cis isomer by reaction with an isomerization catalyst.

In certain embodiments, the process for making 1,1,1,4,4,4-hexafluoro-2-butene (HFO-1336) makes use of an isomerization catalyst which comprises a fluorinated chromia catalyst.

In certain embodiments, the process for making 1,1,1,4,4,4-hexafluoro-2-butene (HFO-1336) further comprises a step of using 1,1,1,4,4,4 hexafluoro-2-butene as a foam blowing agent, a refrigerant, or a solvent.

More particularly, the present invention provides a process for continuously preparing hexafluoro-2-butene (HFO-1336) from 2-chloro-3,3,3-trifluoropropene (HCFC-1233xf) using a specific type of catalyst, preferably a catalyst comprising $Fe_2O_3$/NiO (in about 98 wt % to 2 wt % ratio). A preferred ratio of $Fe_2O_3$ to NiO is from about 95-99 wt % to 5-1 wt % impregnated on carbon; and a reaction temperature of from 600° to 650° C. Other catalysts such as oxides of Ru, Pd or Pt, having properties similar to the preferred $Fe_2O_3$/NiO impregnated on carbon may also be useful in this process.

When other suitable catalysts are employed (for example, $RuO_2$, $RuO_4$ $OsO_4$ in combination with oxides of Pd or Pt (for example, $PdO_2$, $PtO_2$), adjustments to the preferred 600° to 650° C. reaction temperature may be required. The skilled artisan will be able to adjust the reaction conditions using ordinary skill in this art.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

The present invention describes a process for producing HFO-1336 from 2-chloro-3,3,3-trifluoropropene (HCFC-1233xf, $CF_3CCl=CH_2$). HCFC-1233xf is available from many commercial sources or can be obtained by art recognized procedures.

When HCFC-1233xf in the vapor phase is passed over $Fe_2O_3$/NiO (in about 98 wt % to 2 wt % ratio) impregnated on carbon at from 600° to 650° C., the major product identified in the products exit stream is HFO-1336 with $CF_3CH=ClCF_3$ as the minor product. Both the trans and cis isomers of HFO-1336 are formed and the predominant isomer under these conditions was trans (trans/cis=88/12). The trans isomer can be converted into the cis isomer by use of an appropriate isomerization catalyst, such as those described in U.S. Pat. No. 8,426,655.

Under identical vapor phase reaction conditions using other catalysts, (for example, activated carbon pellets)

HCFC-1233xf yielded trifluoropropyne as the major product via dehydrochlorination, with only a trace amount (1-2%) of HFO-1336 being formed.

Thus, by selection of appropriate catalyst, one can get either $CF_3CH\!\!=\!\!CHCF_3$ (HFO-1336) or trifluoropropyne as the major component in the reaction products, as depicted in Scheme 1, below.

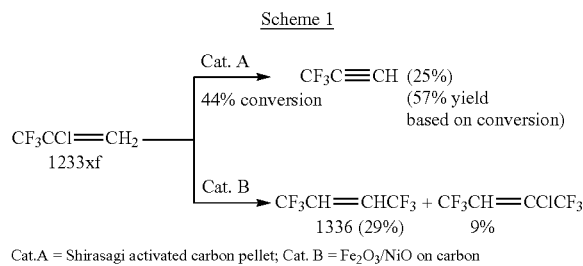

Cat.A = Shirasagi activated carbon pellet; Cat. B = $Fe_2O_3$/NiO on carbon

Although one can rationalize the formation of trifluoropropyne with Cat. A by elimination of HCl from 1233xf, the formation of HFO-1336 with Cat. B as the major product was completely unexpected. Currently, the optimization of the reaction conditions for the above routes to make 1336 or trifluoropropyne has not yet been completed.

The process described here can be carried out in a tubular reactor made of stainless steel or inconel packed with appropriate catalyst with substrate HCFC in vapor phase at elevated temperature. Heating was accomplished by placing the tube reactor in a furnace; generally the portion of the tube containing the catalyst was heated. The reaction/process can be run in a continuous manner. Contact time can vary depending upon the size of the reactor, but includes from about 10 sec to 120 sec, preferably from about 20 sec to 60 sec, and most preferably from about 30 sec to 40 sec.

The preferred catalyst used herein was made by impregnating $Fe_2O_3$ and NiO on activated granular carbon (4-14 mesh). Typically, the catalyst was prepared by mixing an aqueous suspension of $Fe_2O_3$/NiO with 4-14 mesh activated granular carbon. After mixing well, water from the catalyst was removed under reduced pressure.

Isomerization of the trans 1,1,1,4,4,4-hexafluoro-2-butene to its cis isomer can be accomplished using isomerization catalysts like fluorinated chromia as described in U.S. Pat. No. 8,426,655. The isomers can be separated by distillation since boiling points are 9° C. and 33° C. for the trans and cis isomer, respectively.

EXAMPLES

The following examples are merely illustrative of the present invention. They are not to be construed as limitations thereof.

Example 1

Preparation of Catalyst ($Fe_2O_3$/NiO on C)

To 25 mL water 12.6 g $Fe_2O_3$ and 0.25 g NiO was added and mixed well. To this was added 25 cc of granular activated carbon (4-14 mesh) (obtained from Aldrich Co.) mixed well and allowed to stand 4 hours at ambient temperature; water from this catalyst was removed by heating at about 100° C. under reduced pressure (50 to 1 mm Hg).

Example 2

Formation of HFO-1336

Catalyst from Example 1 (15 cm$^3$) was loaded into a tubular Monel reactor (0.5 inch diameter×14 inch length) and slowly heated to and maintained at 650° C. with a nitrogen purge 10-20 sccm. Nitrogen flow was then stopped and 1233xf ($CF_3CCl\!\!=\!\!CH_2$) vapor fed to the tube (flow rate=30 sccm; contact time about 30 sec) was passed over the heated catalyst. The exit stream from the reactor was passed through water, Drierite (drying agent) and collected in a Tedlar bag for GC and GC-MS analyses.

At 650° C., the exit stream from the reactor contained the following (%=area in GC): $CF_3CH\!\!=\!\!CHCF_3$ (29% trans), $CF_3CH\!\!=\!\!CHCF_3$ (4% cis), $CF_3CH\!\!=\!\!CH_2$ (16%), $CF_3Cl$ (16%), $CF_3CH\!\!=\!\!CClCF_3$ (9%) and $CF_3CCl\!\!=\!\!CH_2$ (18%, unreacted). GC-MS data for HFO-1336 (m/e, assignment): 164 $(M)^+$ ($M\!\!=\!\!C_4H_2F_6$), 145 $(M-F)^+$, 95 $(M-CF_3)^+$, 69 $(CF_3)^+$.

Example 3

Reaction of 1233xf with Activated Carbon as the Catalyst

Example 3 was conducted in the same manner as Example 2 except that Shiarasagi pelletized activated carbon (G 2×4/16-1) was used instead of 4-14 mesh granular activated carbon available from Aldrich.

The products identified in the exit stream were the following (GC area %): $CF_3C\!\!\equiv\!\!CH$ (trifluoropropyne) (25%), unreacted $CF_3CCl\!\!=\!\!CH_2$ (56%), $CF_3Cl$ (about 10%) and HFO-1136 (about 2%).

Example 4

Conversion of trans to cis 1,1,1,4,4,4-hexafluoro-2-butene

Hexafluoro-2-butene was passed over at a flow rate of 12 g/h over 20 cc of fluorinated chromia catalyst in a Monel tube reactor (0.5 inch×14 inch) at 250° C.

GC analysis of the exit stream indicated 40% conversion of trans to cis isomer under these conditions. The isomers can be separated by distillation.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making 1,1,1,4,4,4-hexafluoro-2-butene (HFO-1336) from 2-chloro-3,3,3-trifluoropropene (HCFC-1233xf) comprising reacting HCFC-1233xf with a selected catalyst, at a reactive temperature, to produce HFO-1336.

2. The process of claim 1, which is conducted in the vapor phase.

3. The process of claim 2, which is conducted in a continuous manner.

4. The process of claim 2, wherein the catalyst comprises $Fe_2O_3/NiO$.

5. The process of claim 4, wherein the catalyst comprises a ratio of about 95-99 wt % $Fe_2O_3$ to about 5-1 wt % NiO.

6. The process of claim 4, wherein the catalyst comprises a ratio of about 98 wt % $Fe_2O_3$ to 2 wt % NiO.

7. The process of claim 2, wherein the catalyst is selected from the group consisting of $RuO_2$, $RuO_4$, and $OsO_4$ in combination with oxides of Pd or Pt.

8. The process of claim 2, wherein the catalyst is impregnated on carbon.

9. The process of claim 8, wherein the carbon is activated carbon.

10. The process of claim 9, wherein the activated carbon is granular with a mesh size of 4-14.

11. The process of claim 9, wherein the activated carbon is pelletized.

12. The process of claim 2, wherein the reaction temperature ranges from 600° to 650° C.

13. The process of claim 1, wherein both the trans and cis isomers of HFO-1336 are formed.

14. The process of claim 13, wherein the predominant isomer of HFO-1336 formed is the trans isomer.

15. The process of claim 14, wherein the ratio of the trans isomer to the cis isomer of HFO-1336 is about 88:12.

16. The process of claim 15, wherein the trans isomer is converted into the cis isomer by reaction with an isomerization catalyst.

17. The process of claim 16, wherein the isomerization catalyst comprises a fluorinated chromia catalyst.

18. The process of claim 1, further comprising the step of using 1,1,1,4,4,4 hexafluoro-2-butene as a foam blowing agent.

* * * * *